United States Patent
Drescher et al.

(10) Patent No.: US 9,476,842 B2
(45) Date of Patent: Oct. 25, 2016

(54) ON-THE-FLY DIMENSIONAL IMAGING INSPECTION

(71) Applicant: UNITED TECHNOLOGIES CORPORATION, Farmington, CT (US)

(72) Inventors: Joseph D. Drescher, Middletown, CT (US); Eric M. Pedersen, Cheshire, CT (US); Kevin J. Klinefelter, Uncasville, CT (US); Markus W. Fritch, Manchester, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 309 days.

(21) Appl. No.: 14/310,625

(22) Filed: Jun. 20, 2014

(65) Prior Publication Data

US 2014/0300728 A1    Oct. 9, 2014

Related U.S. Application Data

(63) Continuation-in-part of application No. 12/772,510, filed on May 3, 2010, now Pat. No. 8,797,398.

(51) Int. Cl.
| | |
|---|---|
| *H04N 9/47* | (2006.01) |
| *G01N 21/956* | (2006.01) |
| *G01N 21/88* | (2006.01) |
| *G01N 21/95* | (2006.01) |
| *F01D 21/00* | (2006.01) |

(52) U.S. Cl.
CPC ....... *G01N 21/95692* (2013.01); *F01D 21/003* (2013.01); *G01N 21/8806* (2013.01); *G01N 21/9515* (2013.01); *F05D 2270/8041* (2013.01)

(58) Field of Classification Search
USPC ............................................. 348/92
See application file for complete search history.

(56) References Cited

U.S. PATENT DOCUMENTS

| | | | | |
|---|---|---|---|---|
| 4,807,296 | A * | 2/1989 | Ando | G05B 19/408 348/87 |
| 5,125,035 | A * | 6/1992 | McCarthy | G01N 21/95692 348/94 |
| 6,207,946 | B1 | 3/2001 | Jusoh et al. | |
| 7,138,629 | B2 | 11/2006 | Noji et al. | |
| 7,489,811 | B2 * | 2/2009 | Brummel | G01N 21/8806 382/152 |
| 7,574,035 | B2 | 8/2009 | Koonankeil | |
| 2002/0113151 | A1 * | 8/2002 | Forber Jones | B01J 2/02 239/690 |
| 2005/0151963 | A1 * | 7/2005 | Pulla | G01B 21/04 356/139.03 |
| 2007/0276629 | A1 * | 11/2007 | Koonankeil | F01D 5/005 702/185 |
| 2008/0310804 | A1 * | 12/2008 | Brummel | F01D 21/003 385/115 |
| 2010/0188500 | A1 * | 7/2010 | Bouchard | G01N 21/8986 348/93 |

\* cited by examiner

*Primary Examiner* — Dave Czekaj
*Assistant Examiner* — Leron Beck
(74) *Attorney, Agent, or Firm* — Cantor Colburn LLP

(57) ABSTRACT

A method and system are provided for inspecting a plurality of target features arrayed in spaced arrangement on a surface of a target object, such as but not limited to inspection of the location of cooling air holes in the surface of a turbine blade or vane.

20 Claims, 6 Drawing Sheets

ON-THE-FLY DIMENSIONAL IMAGING INSPECTION

CROSS-REFERENCE TO RELATED APPLICATIONS

This patent application is a continuation-in-part of U.S. application Ser. No. 12/772,510, filed on May 3, 2010, entitled "On-The-Fly Dimensional Imaging Inspection."

FIELD OF THE INVENTION

The present disclosure relates generally to systems and methods for inspecting manufactured articles and, more particularly, relates to systems and methods for inspecting multiple features on a manufactured article.

BACKGROUND OF THE INVENTION

Gas turbine engines, such as those used to power modern aircraft, include a compressor for pressurizing a supply of air, a combustor for burning fuel in the presence of high pressurized, compressed air to generate and accelerate high temperature, high velocity combustion gases, and a turbine for extracting energy from the resultant combustion gases. The combustion gases leaving the turbine are exhausted through a nozzle to produce thrust to power the aircraft. In passing through the turbine, the combustion gases turn the turbine, which turns a shaft in common with the compressor to drive the compressor.

As the hot combustion gases pass through the turbine, various turbine elements, such as the turbine stator vanes and turbine rotor blades of the turbine, are exposed to hot combustion gases. In order to protect these turbine elements from exposure to the hot combustion gases, it is known to cool the turbine blades and vanes. In order to facilitate cooling of the blades and vanes, it is known to form the turbine blades and vanes with complex systems of internal cooling passages into which compressor bleed air, or another cooling fluid, is directed to cool the blade or vane. The cooling air exits the blade/vane through a system of holes arranged in such a manner that the exterior surface of the blade/vane is cooled, and is then passed out of the engine with the rest of the exhausted combustion gases.

In some turbine blade/vane embodiments, the cooling air exit holes are arranged in a specific pattern on various facets of the blade/vane airfoil to create a surface cooling film. The surface cooling film creates a layer of cool air, which insulates the airfoil from the hot combustion gases passing through the turbine. In order to ensure that the surface cooling film properly forms, various shaped exit holes are precisely located and drilled at various angles on the surface of the airfoil. Thus, after manufacture it is necessary to inspect the blades and vanes to ensure the holes are properly positioned.

Conventional inspection systems include a fixture for holding the turbine blade/vane being inspected, a video camera, and a computer for controlling the inspection process and processing the video camera images. Generally, conventional inspection systems require inspection of each cooling hole from a gun-barrel view, which typically also requires the use of a five-axis coordinate measuring machine (CMM) for orientating the element and stepping the video probe from hole to hole. Since the turbine vanes and blades may, for example, have as many as 200 to over 300 cooling holes, each cooling hole must be individually inspected.

Conventional inspection systems implement a step and stop process inspection, wherein the video camera is moved from hole location to hole location and positioned in a stationary relationship relative to the hole for a period of about 1.5 to 2.0 seconds before moving on to the next hole. This dwell time is needed for the video camera and the target hole to synchronize position for the video camera to image the target hole, and the computer to analyze the dimensional measurements and output results. The video camera has a low frame rate capability, typically only 30 frames per second. Typically, inspection of a single airfoil may take as long as ten minutes, depending upon the number of holes and also the time required in initial part probing. Part probing is required to properly position the part to be inspected in the workpiece fixture prior to initiating the actual hole inspection, which in conventional practice can take from about 1.5 minutes to over 3 minutes. Therefore, there is a need for improved methods and systems for more quickly determining the location of target features on the surface of a target object.

SUMMARY OF THE INVENTION

In accordance with an aspect of the disclosure, a method is provided for inspecting a plurality of target features arrayed in spaced arrangement on a surface of a target object. The method includes the steps of: providing a fixture for holding the target object; providing a high speed camera; performing a first measurement pass, wherein the first measurement pass includes the steps of: selectively positioning at least one of the holding fixture and the high speed camera relative to the other in an intermittent motion along a three-dimensional path over a plurality of selected target features with stationary pause, and each time the high speed camera orientates to one of the selected target features, capturing a first image and determining a first location of the selected target feature during a first exposure duration using the high speed camera, the high speed camera enabling inspecting of the plurality of selected target features, intermittent stationary pause of the selected target feature relative to the high speed camera over a first duration of a first frame capture resulting in a true position tolerance of the selected target feature; and performing a second measurement pass, wherein the second measurement pass includes the steps of: selectively positioning at least one of the holding fixture and the high speed camera relative to the other in continuous relative motion along the three-dimensional path over the plurality of selected target features without pause, and each time the high speed camera orientates to one of the selected target features, capturing a second image and determining a second location of the selected target feature during a second exposure duration using the high speed camera while in relative motion, the high speed camera enabling inspecting of the plurality of selected target features without pause, movement of the selected target feature relative to the high speed camera over a second duration of a second frame capture being less than a predetermined fraction of the true position tolerance of the selected target feature.

In accordance with another aspect of the disclosure, the method may further include the steps of storing the first captured image and the first determined location of each selected target feature of the plurality of selected target features in a data archive and storing the second captured image and the second determined location of each selected target feature of the plurality of selected target features in the data archive.

In accordance with yet another aspect of the disclosure, the method may further include the step of creating a correction file including respective result locations. Each respective result location being calculated from differences between the first determined location and the second determined location of each selected target feature of the plurality of selected target features.

In accordance with still yet another aspect of the disclosure, the method may further include the steps of providing a next-to-be-inspected target object in the holding fixture and performing a third measurement pass on a plurality of next-to-be-inspected target features arrayed in spaced arrangement on a surface of the next-to-be-inspected target object, wherein the third measurement pass comprises the steps of: selectively positioning at least one of the holding fixture and the high speed camera relative to the other in continuous relative motion along the three-dimensional path over a plurality of selected next-to-be-inspected target features without pause, and each time the high speed camera orientates to one of the selected next-to-be-inspected target features of the plurality of selected next-to-be-inspected target features, capturing a third image and determining a third location of the selected next-to-be-inspected target feature of the plurality of selected next-to-be-inspected target features during a third exposure duration using the high speed camera while in relative motion, the high speed camera enabling inspecting of the plurality of selected next-to-be-inspected target features without pause, movement of the selected next-to-be-inspected target feature of the plurality of selected next-to-be-inspected target features relative to the high speed camera over the third duration of a third frame capture being less than the predetermined fraction of the true position tolerance of the selected target feature.

In accordance with a further aspect of the disclosure, the method may further include the step of creating a report file in the data archive, the report file calculated by combining each determined third location of the selected next-to-be-inspected target feature of the plurality of selected next-to-be-inspected target features and each respective result location in the correction file.

In accordance with an even further aspect of the disclosure, the method may further include the steps of providing a light array in operative association with the high speed camera and each time the high speed camera orientates to one of the selected target features, powering the light array to illuminate the selected target feature during one of the first exposure duration and the second exposure duration.

In further accordance with yet another aspect of the disclosure, the method may further include the step of creating a time-delay file including respective result times. Each respective result time calculated by converting the differences between the first determined location and the second determined location of each selected target feature of the plurality of selected target features.

In accordance with a further aspect of the disclosure, the method may further include the steps of providing a next-to-be-inspected target object in the holding fixture and performing a third measurement pass on a plurality of next-to-be-inspected target features arrayed in spaced arrangement on a surface of the next-to-be-inspected target object without pause, wherein the third measurement pass comprises the steps of: selectively positioning at least one of the holding fixture and the high speed camera relative to the other in a next-to-be-inspected continuous relative motion along the three-dimensional path over a plurality of selected next-to-be-inspected target features without pause, adjusting the high speed camera with the time-delay file, and each time the high speed camera orientates at each respective result time of the time-delay file, capturing a third image and determining a third location of the selected next-to-be-inspected target feature of the plurality of selected next-to-be-inspected target features during a third exposure duration using the high speed camera while in relative motion, the high speed camera enabling inspecting of the next-to-be-inspected target object without pause, movement of the next-to-be-inspected target object relative to the high speed camera over a third duration of a third frame capture being less than the predetermined fraction of the true position tolerance of the selected target feature.

In accordance with an even further aspect of the disclosure, the method may further include the step of storing each third image in a data archive.

In accordance with another aspect of the disclosure, yet another method embodiment is provided for inspecting a plurality of target features arrayed in spaced arrangement on a surface of a target object. The method includes the steps of: providing a fixture for holding the target object; providing a high speed camera; performing a first measurement pass, wherein the first measurement pass comprises the steps of: selectively positioning at least one of the holding fixture and the high speed camera relative to the other in a first continuous relative motion along a three-dimensional path over a plurality of selected target features without pause, the first continuous relative motion moving at a first speed, and each time the high speed camera orientates to one of the selected target features, capturing a first image and determining a first location of the selected target feature during a first exposure duration using the high speed camera while in relative motion, the high speed camera enabling inspecting of the plurality of selected target features without pause, movement of the selected target feature relative to the high speed camera over a first duration of a first frame capture being less than a predetermined fraction of a true position tolerance of the selected target feature; and performing a second measurement pass, wherein the second measurement pass comprises the steps of: selectively positioning at least one of the holding fixture and the high speed camera relative to the other in a second continuous relative motion along the three-dimensional path over the plurality of selected target features without pause, the second continuous relative motion moving at a second speed, the second speed being less than the first speed, and each time the high speed camera orientates to one of the selected target features, capturing a second image and determining a second location of the selected target feature during a second exposure duration using the high speed camera while in relative motion, the high speed camera enabling inspecting of the plurality of selected target features without pause, movement of the selected target feature relative to the high speed camera over a second duration of a second frame capture being less than the predetermined fraction of the true position tolerance of the selected target feature.

In accordance with yet another aspect of the disclosure, the method may further include the steps of storing the first captured image and the first determined location of each selected target feature of the plurality of selected target features in a data archive and storing the second captured image and the second determined location of each selected target feature of the plurality of selected target features in the data archive.

In accordance with still yet another aspect of the disclosure, the method may further include the step of creating a correction file including respective result locations, the respective result locations calculated by extrapolating, to a zero speed, the first determined location and the second determined location of each selected target feature of the plurality of selected target features.

In accordance with a further aspect of the disclosure, the method may further include the steps of providing a next-to-be-inspected target object in the holding fixture and performing a third measurement pass on a plurality of next-to-be-inspected target features arrayed in spaced arrangement on a surface of the next-to-be-inspected target object, wherein the third measurement pass comprises the steps of: selectively positioning at least one of the holding fixture and the high speed camera relative to the other in a next-to-be-inspected continuous relative motion along the three-dimensional path over a plurality of selected next-to-be-inspected target features without pause, the next-to-be-inspected continuous relative motion moving at the first speed, and each time the high speed camera orientates to one of the selected target features of the plurality of selected next-to-be-inspected target features, capturing a third image and determining a third location of the selected next-to-be-inspected target feature of the plurality of selected next-to-be-inspected target features during a third exposure duration using the high speed camera while in relative motion, the high speed camera enabling inspecting of the plurality of selected next-to-be-inspected target features without pause, movement of the selected target feature of the plurality of selected next-to-be-inspected target features relative to the high speed camera over a third duration of a third frame capture being less than the predetermined fraction of the true position tolerance of the selected target feature.

In accordance with an even further aspect of the disclosure, the method may further include the step of creating a report file in the data archive, the report file calculated by combining each determined third location of the selected next-to-be-inspected target feature of the plurality of selected next-to-be-inspected target features and each respective result location in the correction file.

In accordance with still an even further aspect of the disclosure, the method may further include the steps of performing at least a third measurement pass, wherein the at least third measurement pass comprises the steps of: selectively positioning at least one of the holding fixture and the high speed camera relative to the other in a third continuous relative motion along the three-dimensional path over the plurality of selected target features without pause, the third continuous relative motion moving at a third speed, the third speed being less than the second speed, and each time the high speed camera orientates to one of the selected target features, capturing a third image and determining a third location of the selected target feature during a third exposure duration using the high speed camera while in relative motion, the high speed camera enabling inspecting of the plurality of selected target features without pause, movement of the selected target feature relative to the high speed camera over a third duration of a third frame capture being less than the predetermined fraction of the true position tolerance of the selected target feature.

In further accordance with another aspect of the disclosure, the method may further include the steps of storing the first through third captured images of each selected target feature of the plurality of selected target features in a data archive and storing the first through third determined locations of each selected target feature of the plurality of selected target features in the data archive.

In further accordance with yet another aspect of the disclosure, the method may further include the step of creating a correction file including respective result locations, each respective result location calculated by extrapolating, to a zero speed, the first through third determined locations of each selected target feature of the plurality of selected target features.

In accordance with another aspect of the disclosure, yet another method embodiment is provided for inspecting a plurality of target features arrayed in spaced arrangement on a surface of a target object. The method includes the steps of: providing a fixture for holding the target object; providing a high speed camera; providing a light array in operative association with the high speed camera; performing a first measurement pass, wherein the first measurement pass comprises the steps of: selectively positioning at least one of the holding fixture and the high speed camera relative to the other in a first continuous relative motion along a three-dimensional path over a plurality of selected target features without pause, the first continuous relative motion moving at a first speed, and each time the high speed camera orientates to one of the selected target features, capturing a first image and determining a first location of the selected target feature during a first exposure duration using the high speed camera while in relative motion, the high speed camera enabling inspecting of the plurality of selected target features without pause, movement of the selected target feature relative to the high speed camera over a first duration of a first frame capture being less than a predetermined fraction of a true position tolerance of the selected target feature; and performing a second measurement pass, wherein the second measurement pass comprises the steps of: selectively positioning at least one of the holding fixture and the high speed camera relative to the other in a second continuous relative motion along the three-dimensional path over the plurality of selected target features without pause, the second continuous relative motion moving at a second speed, the second speed being less than the first speed, and each time the high speed camera orientates to one of the selected target features, capturing a second image and determining a second location of the selected target feature during a second exposure duration using the high speed camera while in relative motion, the high speed camera enabling inspecting of the plurality of selected target features without pause, movement of the selected target feature relative to the high speed camera over a second duration of a second frame capture being less than the predetermined fraction of the true position tolerance of the selected target feature.

In accordance with still yet another aspect of the disclosure, each time the high speed camera orientates to one of the selected target feature, the light array may be powered to illuminate the selected target feature during one of the first exposure duration and the second exposure duration.

In accordance with an even further aspect of the disclosure, the light array may be a plurality of light emitting diodes in operative association with the high speed camera.

Other aspects and features of the disclosed systems and methods will be appreciated from reading the attached detailed description in conjunction with the included drawing figures. Moreover, selected aspects and features of one example embodiments may be combined with various aspects and features of other example embodiments.

BRIEF DESCRIPTION OF THE DRAWINGS

For a further understanding of the disclosure, reference will be made to the following detailed description which is to be read in connection with the accompanying drawings, where.

DETAILED DESCRIPTION OF THE INVENTION

Figure 1:
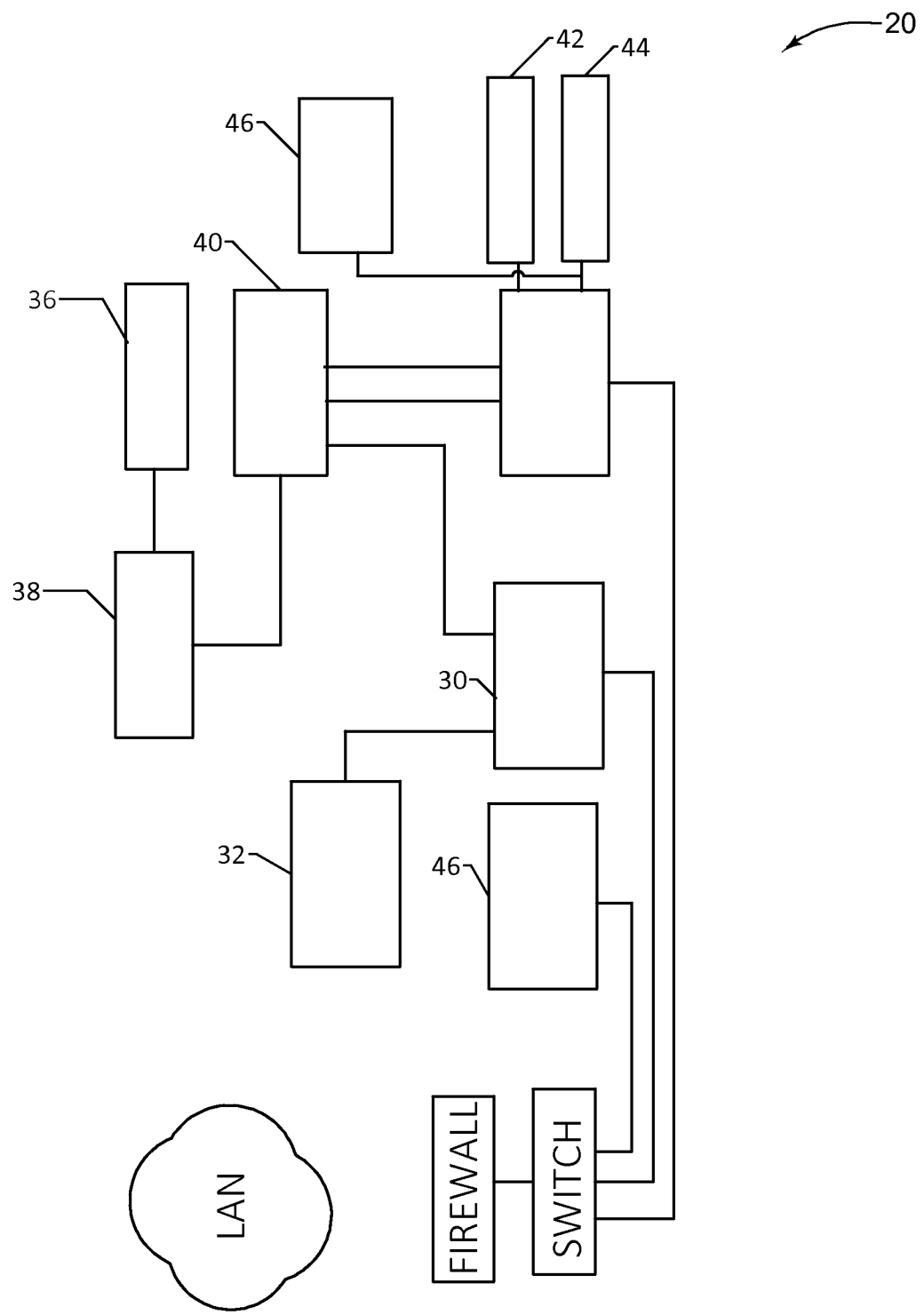
FIG. 1 is a block diagram schematic illustrating an exemplary embodiment of an inspection system for on-the-fly inspection of a plurality of target features associated with a part to be inspected.

There is depicted schematically in FIG. 1 an exemplary embodiment of an inspection system 20 for quickly and accurately locating the position of multiple target features associated with an object to be inspected. For example, the inspection system 20 disclosed herein may be used and the method of inspecting disclosed herein implemented in connection with the inspection of a target object 22. The target object 22 may be, as a non-limiting example, a turbine airfoil, such as a turbine blade or vane shown in FIG. 2. The inspection system 20 may verify the actual location of target features 24 (shown in FIG. 2), such as each of a multiplicity of cooling air exit holes on the surface 26 of the turbine airfoil 22. It is to be understood, however, that the inspection system and the method for inspecting disclosed herein may be adapted for locating other features on other objects.

Figure 2:
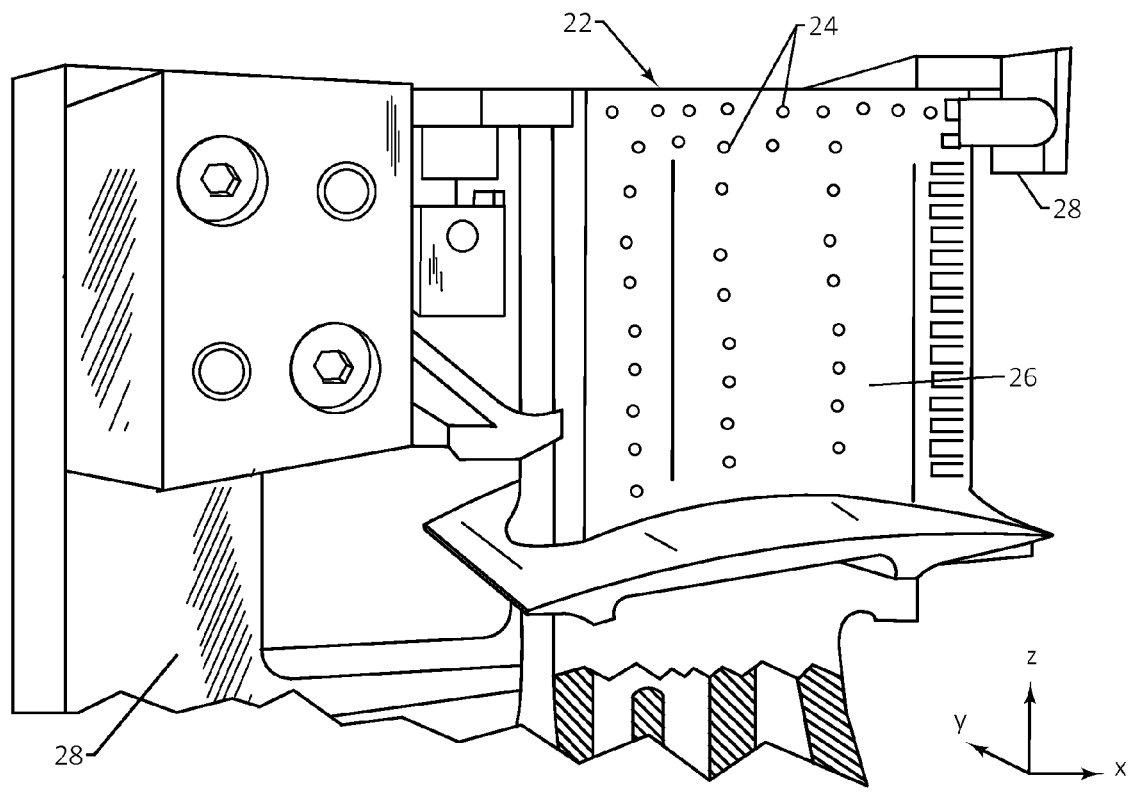
FIG. 2 is a partially cut-away elevation view of the pressure side of a turbine having a multiplicity of cooling air holes.

Referring now to FIGS. 1-2, the inspection system 20 includes a fixture 28 for holding the target part (shown in FIG. 2) being inspected, a fixture position manipulator 30, a controller 32, a processor 34, a light array 36, a light array driver 38 and a high speed camera 40. The holding fixture 28 secures the target part 22 to be inspected in a specific position relative to the holding fixture 28 such that each part in a series of similar parts to be inspected is held in substantially the same position within the holding fixture 28 from part to part. The holding fixture 28 is secured to the fixture position manipulator 30 in a fixed position. The light array 36 is operatively associated with the high speed camera 40 and positioned for providing light on the target part to facilitate imaging of the part by the high speed camera 40. The light array driver 38 is operatively associated with the light array 36 for powering the light array 36 to illuminate the target part. The controller 32 is operatively associated with the fixture position manipulator 30 for commanding the fixture position manipulator 30 to selectively position the holding fixture 28 to orient the target part whereby the selected target feature 24 to be imaged is in a desired orientation relative to the high speed camera 40. The controller 32 also controls positioning of the high speed camera 40 and coordinates the triggering of the high speed camera 40 with the orientation of the target feature such that the high speed camera 40 is triggered and the target feature imaged when the high speed camera is in a gun-barrel shot position with respect to the selected target feature. By gun-barrel shot position/alignment, it is meant that the focal point of the high speed camera 40 is aligned along a line extending normal to the surface of the target object at the location of the target feature to be imaged.

The inspection system 20 is capable of implementing an on-the-fly inspection process in accord with the method disclosed herein. In operation, the controller 32 controls positioning of the target part by manipulation of the fixture position manipulator 30 in a controlled coordinated manner with movement of the high speed camera 40 whereby continuous relative movement along a specified, arbitrary three-dimensional path over the plurality of selected target features to be imaged is maintained between the high speed camera 40 and the target part as the multiplicity of target features are imaged without pause. That is, the high speed camera does not stop and dwell over any target feature location during imaging of that location on the target part. Rather, in accord with the process disclosed herein, the high speed camera 40 and the selected target feature to be imaged are in relative motion at a constant speed as the high speed camera is triggered and images the selected target feature. By eliminating the dwell time over the part at each inspection site, the inspection time associated with inspecting an individual target feature, such as a cooling air hole on a turbine airfoil, is significantly reduced relative to the conventional step and stop inspection method.

In on-the-fly inspection as disclosed herein, the movement of the target feature of interest relative to the high speed camera 40 over the duration of the frame capture must be less than a reasonable fraction, such as for example $\frac{1}{10}^{th}$, of the true position tolerance of the target feature. Thus, in implementing the on-the-fly inspection method disclosed herein, the speed of movement of the high speed camera 40 is primarily limited by the frame rate capability of the camera 40 and the ability of the high speed camera 40 to collect enough light during the exposure duration for adequate contrast so that the image of the target feature can be resolved. Generally, the high speed camera 40 should have an exposure duration, i.e. time required for imaging a target feature, of less than three (3) milliseconds. For example, a high speed camera having a frame rate capability of at least about 300 frames per second would enable imaging with relative motion between the camera and the target feature at a constant speed of at least about 50 inches per minute.

The light array 36 is provided for illuminating the target feature with sufficient light at least during the exposure duration, that is at the time the high speed camera 40 images the target feature. The light array 36 comprises a plurality of high intensity light emitting devices, for example light emitting diodes (LEDs), arranged to illuminate the target feature to provide adequate contrast. The number of light emitting diodes comprising the light array 36 depends upon the power level applied to drive each diode. If a higher power level is applied per diode, for example about one watt or more per diode, the number of light emitting diodes may be decreased. Conversely, if a lower drive power level per diode is desired, a greater number of light emitting diodes may be provided. However, conventional low power, i.e. low wattage, LEDs commonly used in commercial applications do not provide sufficient light output per diode to be used in implementing the on-the-fly inspection method disclosed herein. The number of LEDs may also be reduced if a means of focusing is provided in association with the light emitting devices forming the light array 36 to increase the flux (intensity per unit area) in the image field of view of the high speed camera 40. The LEDs making up the light array 36 may be arranged in a ring pattern, in a single row, a double row or any other suitable arrangement.

The light array driver 38 is controlled by the controller 30 through the high speed camera 40 to power the light emitting devices comprising the light array 36. Although the light array could be powered continuously during the inspection process, doing so creates excess heat and shortens the life of the lights. In implementing the method disclosed herein using a high speed camera, the light array 36 may be powered in synchronization with the imaging of the target feature by the high speed camera 40. When the high speed camera 40 is moving over the target feature, the high speed camera 40 triggers the light driver 38 to power the light array 36 to illuminate the target feature during the exposure duration. With LEDs making up the light array 36, the light driver 38 comprises a LED driver having the capability of selectively switching the light array LEDs from zero power to at least full power in less than one microsecond to flash the LEDs in coordination with the camera exposure duration. Precise coordination of the camera exposure duration and the LED flash duration is particularly important at the higher relative speeds of movement between the high speed camera 40 and the target feature to be imaged that may be used in implementing the on-the-fly inspection method disclosed herein to eliminate blurring and ensure clarity of the image of the target feature.

Additionally, the LED driver can have the capability of over-powering the light array LEDs, that is powering individual LEDs of the light array 36, all or selected LEDs thereof, at a power level in excess of the full rated power of the LED. Although over-powering the LEDs is not required when implementing the on-the-fly inspection method disclosed herein, over-powering the LEDs produces a "strobing-like" effect that may improve image contrast and clarity during the exposure duration. This effect is not possible to attain with conventional lights, such as incandescent or halogen lights. The light array LEDs are arranged such that directional control is available for adjustment of the geometry comprising the orientation of the optical axis of the camera lens, the light from the LEDs, and the target part orientation surrounding the feature of interest. Adjustment may be achieved by selectively controlling, through software control, the intensity of each available light array LED at its respective location with respect to the target feature.

As noted previously, conventional step and stop inspection systems typically employ a 5-axis, coordinate measuring machine in combination with a low speed video camera. Such machines can move the video camera and/or the part to a location and orientation very well in a step and stop inspection process even though each axis may arrive at its individual target location at a different time. However, conventional coordinate measuring machines do not have the ability to control three linear and two rotary axes in a coordinated fashion for imaging while in motion as required in implementation of the on-the-fly inspection method disclosed.

In the on-the-fly inspection system 20, the fixture position manipulator 30 comprises a computer numerically controlled (CNC) machine under direct control of the controller 32. The CNC machine 30 secures the fixture 28 that holds the target object to be inspected. The CNC machine 30, under the control of the controller 32, provides coordinated five degree of freedom motion control for maneuvering the fixture 28 in the CNC machine 30 to align the target object to a desired orientation with the high speed camera 40 for imaging of the selected target feature. CNC machines with coordinated 5-axis motion control are known for use in the aerospace industry for machining applications, for example where the location and orientation of a cutting tool relative to the workpiece is important at all times when the two are in contact. However, the use of CNC machines with coordinated five degrees of freedom motion control is novel in inspection applications for imaging a target feature on a target object with a high speed camera while in relative motion along a three-dimensional path without the stop and step required in practice.

As noted above, in on-the-fly inspection as disclosed herein, the high speed camera 40 images the target feature while in relative motion with respect to the selected target feature at a constant speed. Depending upon the relative speed and the spacing between target features, the high speed camera 40 may be imaging several target features a second. Therefore, the inspection system must be capable of handling the images produced in such a manner as to not adversely impact control loop cycle time of the controller 32. During a single control loop cycle, the computer 34 will receive a signal from feedback devices of each axis as the actual position, modify this position of each axis with any active corrections as applicable, compare the result to the commanded position at that time, and output power signals to each axis motion control device (usually a motor) associated with the fixture position manipulator 30 subject to the various control parameters (tuning) which have been set. The control loop cycle time should desirably be around 1 millisecond or less. Performing analysis of images and performing other output functions during the "random" cycles when the images are available (1 in 150 cycles for example) in such a way that the cycle time can be maintained reliably would severely limit what the cycle time could be achieved and consequently may limit the speed of measurements.

Accordingly, the inspection system 20 incorporates a parallel processor 34 for performing image analysis. Whenever the high speed camera 40 images a target feature, the single frame image is captured by the high speed camera 40 and stored to memory as a file in data archive 42. The processor 34 will access the image file, read the image file, analyze the image, determine the location of the target feature, for a hole center, and create the output data while the high speed camera and target object are in motion to align on the next target feature of interest. In conventional stop and step inspection methods, the image analysis was performed while the video camera remained stationary in front of the imaged target feature. In the on-the-fly inspection method disclosed herein, the image analysis occurs while the high speed camera and the target object are in relative motion along a three-dimensional path at its constant speed as the next target feature is brought into a gun-barrel shot alignment with the high speed camera. Therefore, image analysis does not adversely impact control loop cycle time. If desired, an additional processor 46 may be provided in parallel with the processor 34 to assist in processing the images. Each of the processors 34 and 46, as well as the controller 30, may be commercially available microprocessors, each of which is typically associated with a separate computer monitor, memory bank and peripherals, but two or more of which may be associated with a common computer monitor, memory bank and peripherals, if practical from a logistics and processing viewpoint.

As an exemplary embodiment, the on-the-fly inspection method will be described further as implemented for the inspection of turbine airfoils for the purpose of verifying the position of a multiplicity of cooling air holes. Referring to FIG. 2, there is depicted an exemplary embodiment of a turbine airfoil 22 having a multiplicity of cooling air exit holes 24 arranged generally in a column and row fashion on the pressure side surface 26 of the airfoil 22. The root or bottom of the airfoil 22 is shown in cut-away to reveal cooling air passages 48. To cool the turbine airfoils during operation of the gas turbine engine, high pressure air, typically compressor bleed air, enters the cooling passages 48, which extend into the interior of the turbine airfoil 22. At least a portion of the cooling air exits from the cooling air passages 48 through the cooling air exit holes 24 to flow along the exterior surface of the turbine airfoil 22. The multiplicity of cooling air exit holes 24 must be arranged in a precise pattern designed to achieve complete cooling coverage of the surface of the turbine airfoil 22. In an exemplary embodiment of a turbine airfoil, over 300 cooling air exit holes 24 may be provided with the cooling air exit holes 24 typically having a diameter of about 300 microns and typically being spaced apart at about 0.200 inches.

The on-the-fly inspection method disclosed herein can be used for verifying the precise actual location of each cooling air exit hole 24 on the turbine airfoil 22. To begin, through the user interface, which may be a dedicated computer terminal or a computer terminal in a network system, the operator selects the appropriate program for the turbine airfoil (blade or vane) to be inspected from a list of available part programs. The airfoil to be inspected, for example turbine airfoil 22, is loaded in a known manner in the fixture 28 of the fixture position manipulator 30, which in this implementation of the method comprises a five degree of freedom CNC machine. The high speed camera 40 and the holding fixture 28 are supported in the CNC machine 30 in spaced, facing relationship. The high speed camera 40 may be supported for movement in one or two linear degrees of freedom, while the holding fixture 28 is supported for movement in both rotational degrees of freedom and at least one linear degree of freedom. In a typical installation, the high speed camera 40 would be supported above the fixture and at least moveable along a vertical axis up and down relative to the turbine airfoil held in the holding fixture 28. With a turbine airfoil loaded onto the CNC machine 30, the location and orientation of the turbine airfoil with respect to each of the five degrees of freedom of the CNC machine 30 can be estimated based on the design of the holding fixture 28. As in conventional systems, the design of the holding fixture 28 includes the fixing of the turbine airfoil 22 to the holding fixture 28 in a repeatable consistent manner from airfoil to airfoil as well as the means of fixing the holding fixture 28 to the CNC machine 30 in a consistent manner.

It is difficult to know the location and orientation of the turbine airfoil with respect to the CNC machine to a level of accuracy required for the measurement of feature locations. This is due to the influence of variations that arise from actual dimensions of the turbine airfoil and holding fixture within their respective machining tolerances as well as the non-repeatability of airfoil loading and fixture loading. Because of the careful design and process controls that would be required to position the part deterministically to within the required limits, a touch-trigger probe is used to simply find the actual location and orientation of each individual turbine airfoil prior to its measurement. The part datum planes are established by measuring the location of 6 specific points on the surface of the turbine airfoil.

In conventional practice for hole inspection on turbine airfoils using the step and stop method, the accurate determination via part probing usually involves multiple iterations of the 6-point probing sequence for which each successive sequence improves accuracy in the determination of the part location and orientation. Iterations are required due to curvature on the surface in the vicinity of the specified datum points. If there is no curvature of the surface in the vicinity of the datum points, it is feasible to find the location and orientation of the part in one iteration of the probing sequence. In existing applications, part probing consumes from a tenth to a third of the total measuring time. It is a fixed time so the percent of total depends on the number of holes to be inspected, which is the variable time depending on individual part program.

However, if the same conventional part probing methods were to be used when implementing the on-the-fly inspection method disclosure herein for turbine airfoil cooling air hole inspection, the part probing portion of the measurement cycle could be expected to approach 75% even when a turbine airfoil has a relatively high number of holes to be inspected. Therefore, to shorten overall inspection time and take full advantage of the time saving associated with on-the-fly inspection, when implementing the on-the-fly inspection method the nominal location and orientation of a turbine airfoil loaded into the CNC machine 30 will be what was found as the actual location and orientation of the most previous turbine airfoil inspected, thereby reducing the potential variation to only the repeatability of the part loading and the variation within tolerances of the locating surface of the part. Additionally, the touch-trigger probe to be used will consist of two distinctly calibrated positions. The first position being the sphere at the end of the stylus and the second position being the cylinder of the stylus shaft itself at a specified location up from the sphere center. When the calibrated cylindrical portion of the probe is used on a surface datum point having curvature, it creates a line/point contact and eliminates errors due to curvature in one direction. Further, prior to initiation the probing sequence of the 6 datum points, a single point will be probed to establish a very good estimate of the turbine airfoil location along the part Z-axis. These changes will reduce the required probing to a single iteration for most parts and reduce the probing time from around 100 seconds associated with conventional probing practices to less than 50 seconds.

Figure 3:
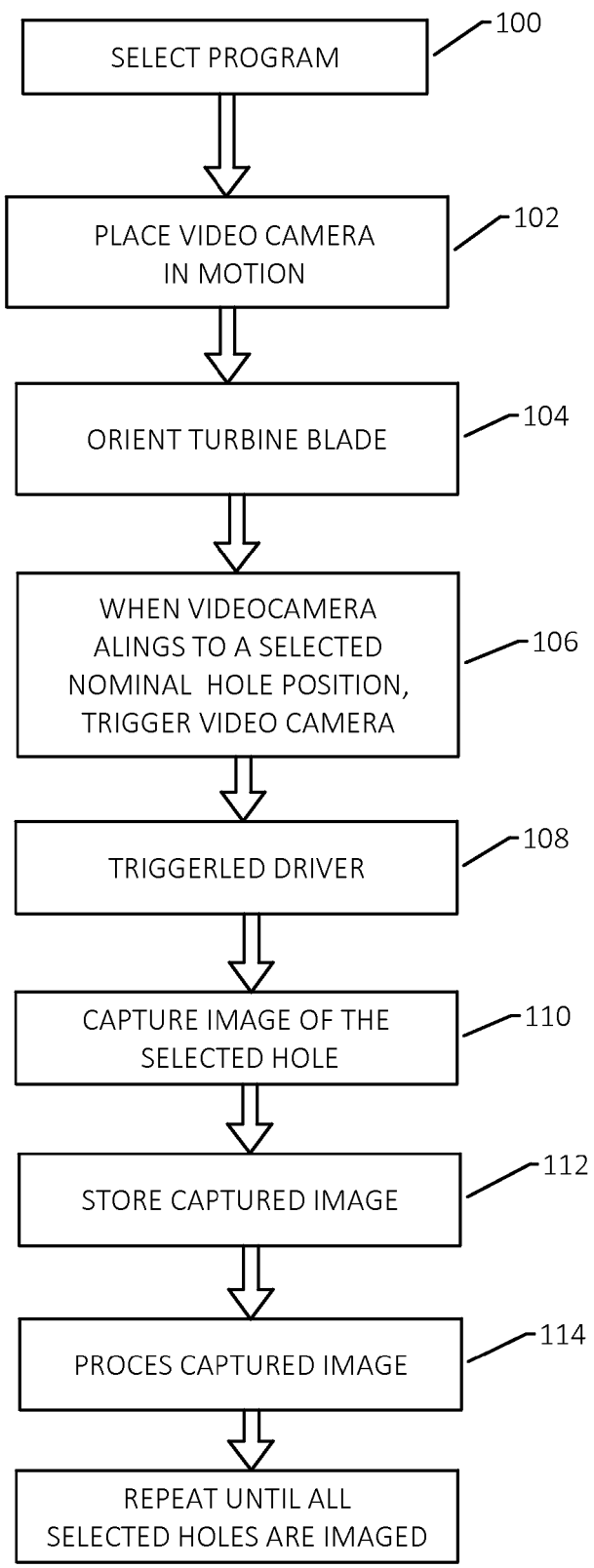
FIG. 3 is a flow chart illustrating a method for on-the-fly inspection in accord with an aspect of the invention.

Referring now to FIG. 3, when the operator selects the appropriate program associated with the turbine airfoil to be inspected, at step 100, the selected program will be loaded into the controller 32. The program will consist mainly as a list of positions for each of the 5 degrees of freedom associated with the CNC machine 32, i.e. 3 linear degrees of freedom (x, y and z coordinate axes) and two rotational degrees of freedom (one about the axis of the holding fixture and one in a plane orthogonal to the axis of the holding fixture). These positions correspond to the nominal locations of the holes to be inspected. The camera settings for the high speed camera 40, which in this implementation of the method disclosed herein comprises a video camera, are configurable by the data link with the controller 32. When a part program is selected, the controller 32 will make the previously specified settings on the video camera for that particular part program.

The actual inspection cycle begins with the computer, at step 102, placing the video camera 40 in motion and, simultaneously at step 104, maneuvering the fixture 28 holding the turbine airfoil. The video camera 40 and turbine airfoil are in relative motion along a three-dimensional path at a constant relative speed to orient the turbine airfoil and the video camera such that the next to be imaged target hole and the video camera are brought into gun-barrel shot alignment. For example, the video camera and the turbine airfoil may be in relative motion along a three-dimensional path at a constant relative speed of at least about 50 inches per minute between holes in a row/column of holes 24 and at an even higher relative speed, for example about 200 inches per minute, between rows/columns of holes 24. The controller 32 controls the CNC machine 30 to maneuver the fixture 28 and relative movement of the video camera to properly orient the turbine airfoil 22 with respect to the video camera 40 for imaging of each individual hole 24 of the multiplicity of cooling air holes 24 on the surface of the turbine airfoil 22.

At step 106, at each instant during the inspection cycle that the video camera 40 aligns in gun-barrel shot relationship to a nominal hole position, the controller 32 sends a signal to the video camera 40. At step 108, upon receipt of that signal from the controller 32, the video camera 40 triggers the LED driver 38 which in turn powers, that is switches from zero power to full power, the LEDs of the light array 36 for a preset duration. At step 110, in synchronization with the flashing of the LEDs of the light array 36, the video camera 40 captures an image of the target hole 22 as the video camera passes over the target hole.

At step 112, the captured image is stored in a designated folder in the data archive 42 associated with the processor 34. At step 114, the captured image is accessed and processed in parallel with the movement of the video camera 40 and the maneuvering of the fixture 28 while repositioning at a constant relative speed toward the next target hole. The basic result of an image analysis will be the pixel location of the centroid of the identified blob (Binary Large Object), i.e. the cooling air exit hole 24. Based on previous calibration the location and rotation of the camera pixel array is known with respect to the machine coordinate system. Also, the location and orientation of the part coordinate system is known with respect to the machine coordinate system by the nominal tool design and by the results of the part probing which refines the tool matrix to actual. Furthermore, the location and orientation of each hole 24 is specified by the engineering definition for the part with respect to the part datum planes. Appropriate coordinate transformations are carried out by the processor 34 to determine the location of each hole 24 relative to that hole's nominal, specified location. The difference is the true position error.

The on-the-fly inspection method disclosed herein is capable of performing a hole location inspection of a turbine airfoil several times faster than the time required for using conventional step and stop hole inspection methods. For example, a turbine vane having 211 holes was subject to hole measurement inspection using a conventional step and stop method using a video camera having a frame rate capability of 30 frames per second. The time required to measure all of the 211 holes was timed at 443 seconds. Implementing the on-the-fly method disclosed herein using a high speed video camera having a frame rate capability of 1000 frames per second and moving the video camera and maneuvering the orientation of the turbine airfoil at a constant relative speed of 50 inches per minute between holes in a row and at a speed of 200 inches per minute between rows, it is estimated the measurement time for measuring the same 211 holes would be reduced to 43 seconds, a ten-fold decrease. As a further example, a turbine airfoil having 330 holes was subject to hole measurement inspection using a conventional step and stop method using a video camera having a frame rate capability of 30 frames per second. The time required to measure all of the 330 holes was timed at 690 seconds. Implementing the on-the-fly method disclosed herein using a high speed video camera having a frame rate capability of 1000 frames per second and moving the video camera and maneuvering the orientation of the turbine airfoil at a constant relative speed of 50 inches per minute between holes in a row and at a speed of 200 inches per minute between rows, it is estimated the measurement time for measuring the same 330 holes would be reduced to 57 seconds, an over ten-fold decrease.

Due to the dynamics of the CNC machine and the timing of electrical components, the on-the-fly inspection method discussed herein may be slightly less accurate, but within appropriate tolerances, in determining actual hole location on turbine airfoils as the conventional stop-and-dwell inspection method. However, the synergistic effect of the combination of the high speed camera, the five degree of freedom CNC machine, the LED light array and the controller for coordinating the relative motion along a three-dimensional path between the high speed camera and the turbine with the triggering of the high speed camera to image the holes while in relative motion, provides for a much faster inspection method, more than offsetting a slight difference in accuracy. Furthermore, any slight deficiency in accuracy compared to the conventional "stop and dwell" method may be compensated for on a part by part basis.

For example, for each unique part number to be inspected, a master part is identified as a calibrated artifact. The master part is then measured on a conventional inspection apparatus in accord with a conventional "stop and dwell" method. The master part is also measured on an inspection system implementing the "on-the-fly" inspection method disclosed herein. The respective hole dimension results attained by the two methods are compared for each and every measured hole location. A table of the differences is created and loaded into the inspection program for the on-the-fly method as a x-axis correction value and a y-axis correction value for each hole location. For each subsequent part with this unique part number inspected, the appropriate correction values will be added to the actual measured dimensional values thereby "correcting" for the output results from the on-the-fly inspection method disclosed herein to conform to the conventional "stop and dwell" method, whereby accuracy of measurement does not suffer, but significant time savings are achieved.

Figure 4:
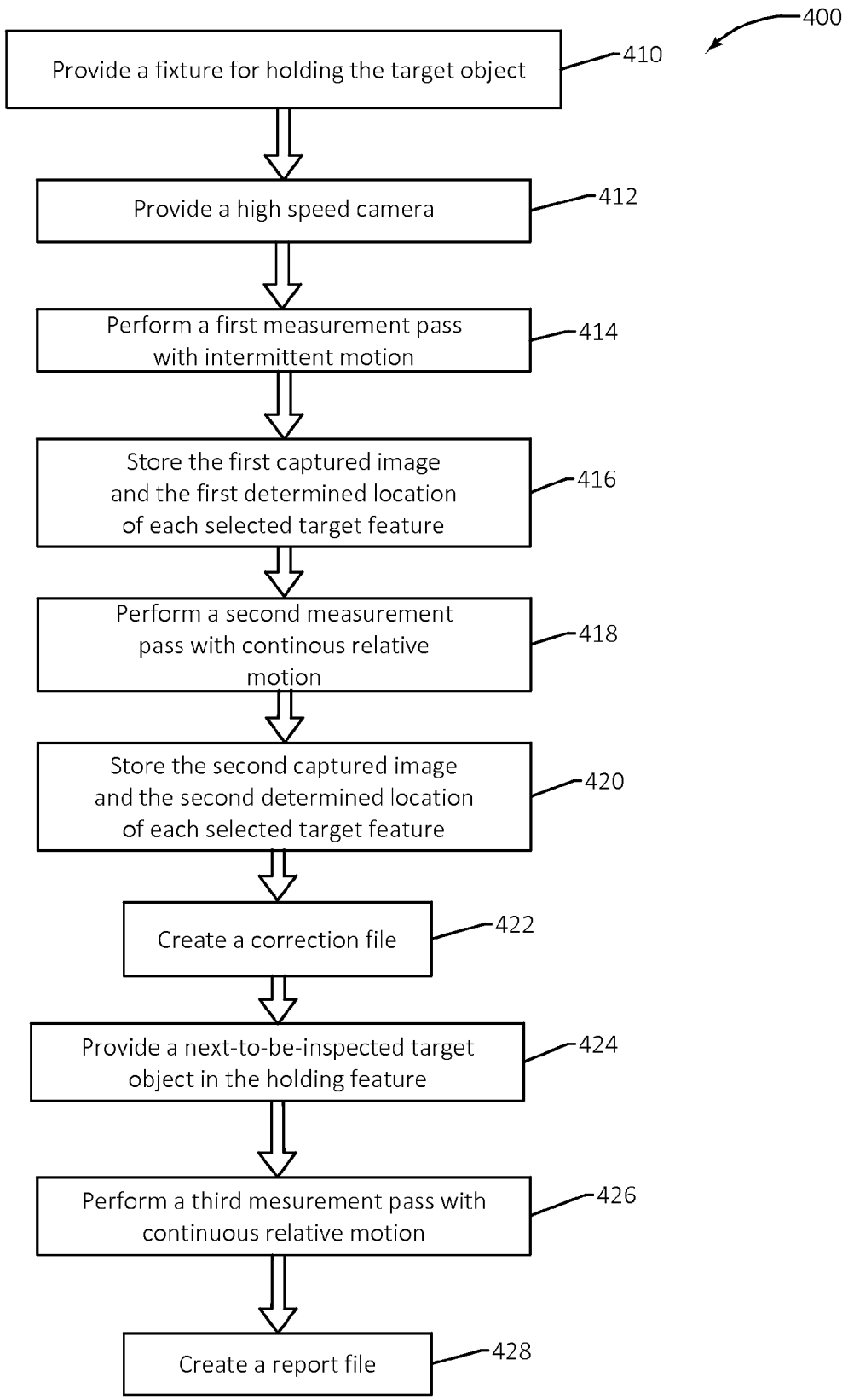
FIG. 4 is a flow chart illustrating an alternative embodiment of a sample sequence of steps which may be practiced in accordance with the teachings of this disclosure.

Referring to FIG. 4, a flow chart 400 is shown depicting an alternative embodiment of a sample sequence of steps that may be performed to inspect the plurality of target features 24 on the target object 22. Similarly, as described above, in this embodiment, a fixture 28 for holding the target object 22 is provided along with a high speed camera 40, as illustrated in boxes 410 and 412. Another step, as shown in box 414, is performing a first measurement pass on the target object 22 using the "stop and dwell" method described above. During the "stop and dwell" measurement pass, either the holding fixture 28 or the high speed camera 40 is in intermittent motion relative to the other. In particular, the high speed camera 40 is selectively oriented to each target feature of the plurality of target features 24 for a stationary pause period before moving onto the next target feature to be measured. As depicted in box 416, this stationary pause over each target feature allows the camera 40 to capture an image of each target feature, which may be stored as a file in the data archive 42. The processor 34 may access each image file of each target feature, read each image file, analyze each image file, determine the location of each target feature, and create data output of the location of each target feature. The data output may be stored in the data archive 42.

As depicted in box 418, the target object 22 may then be measured by performing a second measurement pass using the on-the-fly inspection method, which was described above. As a brief overview, during the on-the-fly inspection method either the holding fixture 28 or the high speed camera 40 is in continuous motion relative to the other. The high speed camera 40 is selectively oriented to each target feature of the plurality of target features 24 without pause allowing the high speed camera 40 to capture an image of each target feature, which may also be stored as a file in the data archive 42, as illustrated in box 420. The processor 34 may access each image file of each target feature, read each image file, analyze each image file, determine the location of each target feature, and create data output of the location of each target feature. The data output may be stored in the data archive 42. Although the "stop and dwell" method pass was described as being performed before the on-the-fly inspection method pass, the order may be reversed so that the on-the-fly inspection method pass may be performed before the "stop and dwell" method pass.

As shown in box 422, the processor 34 may create a correction file calculated from the differences between the result locations (data output) for each respective target feature attained by the two measurement passes. The correction file may also be stored in the data archive 42.

The step of providing a next-to-be-inspected target object in the holding fixture 28 is illustrated in box 424. Once the next-to-be-inspected target object is secured in the holding fixture, a third measurement pass using the on-the-fly inspection method may be performed on the next-to-be-inspected target object having a plurality of next-to-be-inspected target features, as depicted in box 426. The processor 34 may access each captured image file of each next-to-be-inspected target feature produced from the third measurement pass, and read each image file, analyze each image file, determine the location of each next-to-be-inspected target feature, and create an inspection file of the location of each next-to-be-inspected target feature. The inspection file may also be stored in the data archive 42. As depicted in box 428, a report file may be created, by the processor 34, of the calculated differences between the inspection file and the correction file.

Figure 5:
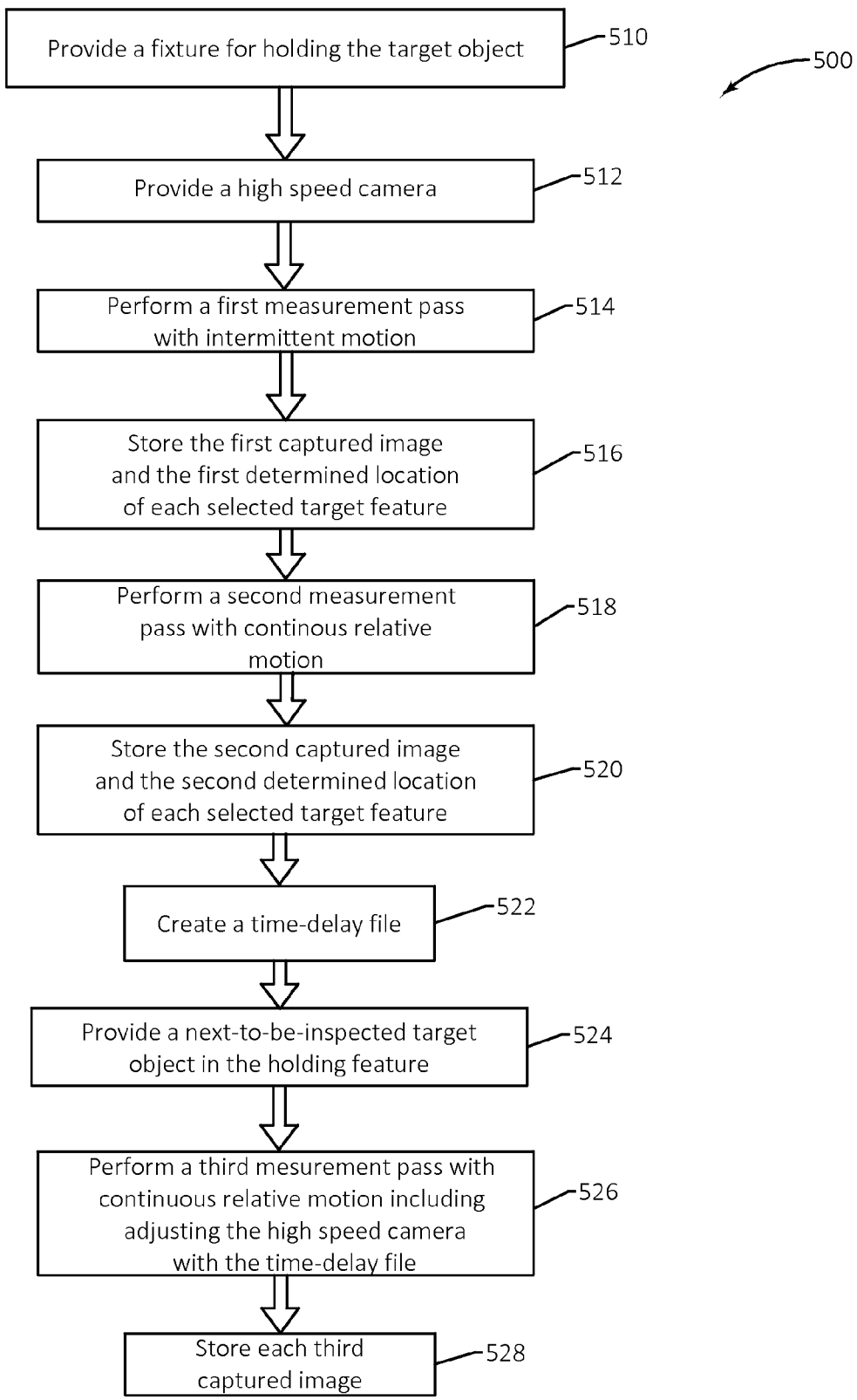
FIG. 5 is a flow chart illustrating another alternative embodiment of a sample sequence of steps which may be practiced in accordance with the teachings of this disclosure.

Turning now to FIG. 5, a flow chart 500 is shown depicting another alternative embodiment of a sample sequence of steps that may be performed to inspect the plurality of target features 24 on the target object 22. As seen in boxes 510 and 512, this embodiment is similar to the embodiment depicted in FIG. 4 in that a fixture 28 for holding the target object 22 is also provided along with a high speed camera 40. This embodiment also performs a first measurement pass using the "stop and dwell" method, as depicted in box 514, and stores a captured image of each target feature 24 and similarly determines the location of each target location.

As shown in boxes 518, a second measurement pass using the on-the-fly inspection method is performed. In this second measurement pass, as depicted in box 520, the stored captured image of each target feature 24 allows the processor 34 to determine a second location of each target feature 24. Similar to the embodiment of FIG. 4, the second measurement pass may be formed before the first measurement pass.

Instead of creating a correction file like the embodiment of FIG. 4, the processor 34 may create a time-delay file including respective result times. Each respective result time is calculated by converting, into a time based on a known speed, the differences between the first determined location and the second determined location of each selected target feature of the plurality of selected target features. The known speed may be the same speed used during the on-the-fly inspection pass, and as a non-limiting example, may be 50 inches per minute.

A next-to-be-inspected target object may be provided in the fixture 28 and a third measurement pass may be performed, as illustrated in boxes 524 and 526. The third measurement pass is performed using the on-the-fly method having the high speed camera 40 adjusted by the time-delay file so that the high speed camera 40 captures a third image at each respective result time of the time-delay file. Each captured third image may be stored in the data archive 42, as exemplified in box 528. Each third image is, thus, corrected by the time-delay file.

Figure 6:
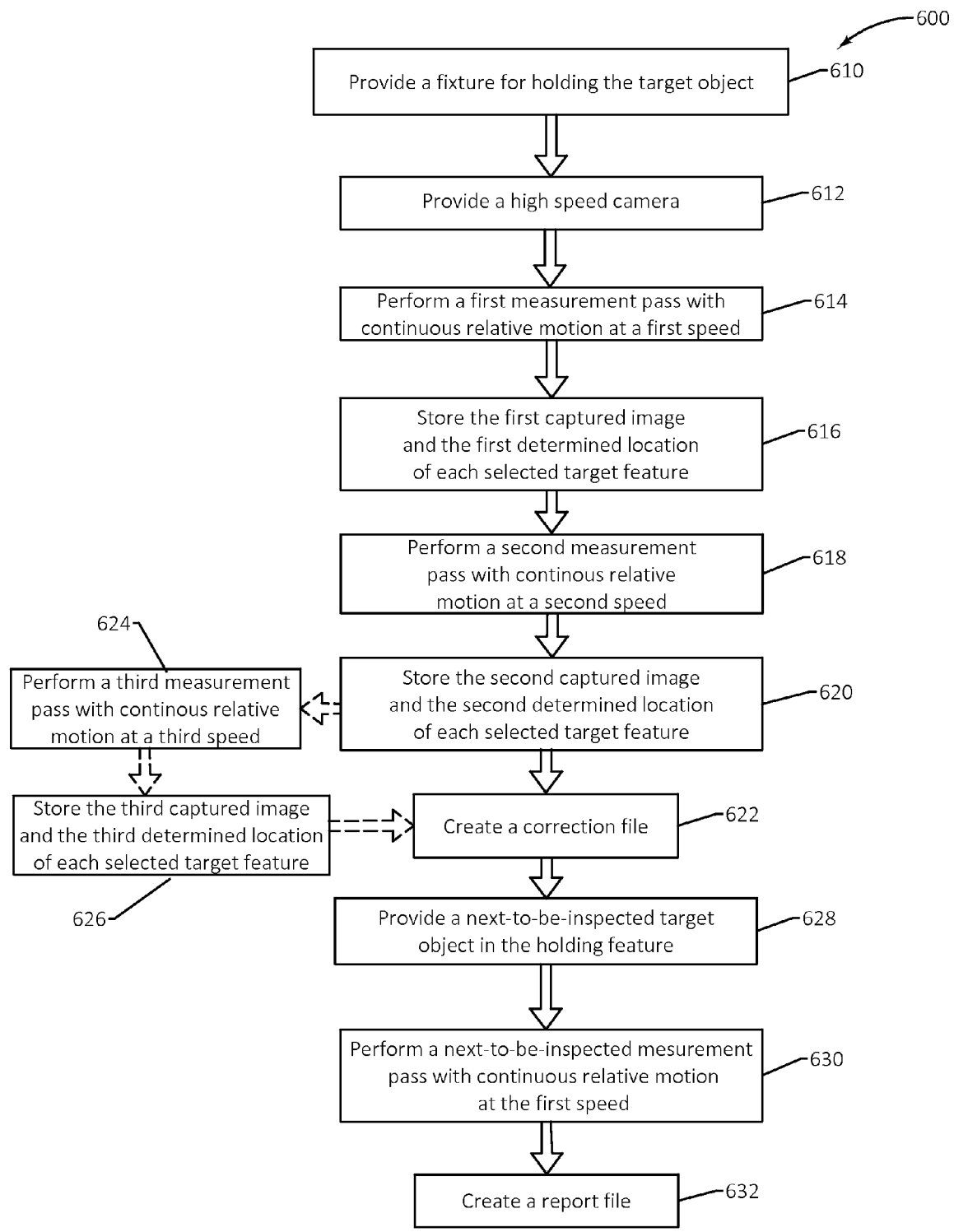
FIG. 6 is a flow chart illustrating yet another alternative embodiment of a sample sequence of steps which may be practiced in accordance with the teachings of this disclosure.

Another example embodiment is depicted in the flow chart 600 of FIG. 6. As shown in boxes 610 and 612, this embodiment also provides a fixture 28 for holding the target object 22 having a plurality of target features 24 and a high speed camera 40. In this embodiment, as depicted in box 614, a first measurement pass is performed using the on-the-fly inspection method. During the first measurement pass either the fixture 28 or the high speed camera 40 is in continuous relative motion relative to the other, as previously discussed. The continuous relative motion moves at a first speed. For example, the first speed may be at a one hundred percent capability of motion. Similar to the other embodiments, as illustrated in box 618, the high speed camera 40 is selectively oriented to each target feature of the plurality of target features 24 without pause allowing the high speed camera 40 to capture an image of each target feature, which may also be stored as a file in the data archive 42, and allow the processor 34 to access each image file of each target feature, read each image file, analyze each image file, determine the location of each target feature, and create data output of the location of each target feature. The data output may be stored in the data archive 42.

Box 618 illustrates the step of performing a second measurement pass over the target object 22. In this embodiment, both the first and second measurement passes are performed using the on-the-fly inspection method. This differs slightly from the previously mentioned embodiments in which their first and second measurement passes included an on-the-fly pass and a "stop and dwell" pass. The continuous relative motion involved in the second measurement pass, however, is performed at a second speed that is a fractional speed less than the first speed. For example, the second speed may be at 50% capability of motion. At this second speed, the high speed camera 40 is selectively oriented to each target feature of the plurality of target features 24 without pause allowing the high speed camera 40 to capture an image of each target feature, which may also be stored as a file in the data archive 42, as exemplified in box 620, and allow the processor 34 to access each image file of each target feature, read each image file, analyze each image file, determine the location of each target feature, and create data output of the location of each target feature. The data output may be stored in the data archive 42.

As shown in box 622, the processor 34 may create a correction file including respective result locations. The respective result locations may be calculated by extrapolating the result locations (data output) for each respective target feature attained by the two measurement passes in order to approximate the respective result locations at a zero speed. The correction file may also be stored in the data archive 42. It is possible, however, that the result locations attained from the first and the second measurement passes may not be linear with speed, in which case a third measurement pass using the on-the-fly inspection method at a third speed may need to be taken, as exemplified in boxes 624 and 626. The third speed may be a fractional speed less than the second speed. For example, the third speed may be at 10% or 25% capability of motion. With the result locations of the three passes, the correction file may be calculated by extrapolating with a quadratic or higher order curve fitting to a zero speed instead of the linear extrapolation with the result locations of the two passes.

A next-to-be-inspected target object may be provided in the fixture 28 and a next-to-be-inspected measurement pass may be performed, as illustrated in boxes 628 and 630. The next-to-be-inspected measurement pass is performed using the on-the-fly method having the continuous relative motion moving at the first speed. The processor 34 may access each captured image file of each next-to-be-inspected target feature produced from the next-to-be-inspected measurement pass, and read each image file, analyze each image file, determine the location of each next-to-be-inspected target feature, and create an inspection file of the location of each next-to-be-inspected target feature. The inspection file may also be stored in the data archive 42. As depicted in box 632, a report file may be created, by the processor 34, of the calculated differences between the inspection file and the correction file.

The terminology used herein is for the purpose of description, not limitation. Specific structural and functional details disclosed herein are not to be interpreted as limiting, but merely as basis for teaching one skilled in the art to employ the present invention. Those skilled in the art will also recognize the equivalents that may be substituted for elements described with reference to the exemplary embodiments disclosed herein without departing from the scope of the present invention.

While the present invention has been particularly shown and described with reference to the exemplary embodiment as illustrated in the drawing, it will be recognized by those skilled in the art that various modifications may be made without departing from the spirit and scope of the invention. For example, in the implementation of the inspection method described herein, the inspection measures the hole location in two dimensions. However, in other applications, the method could be used to measure hole size or the orientation of the axis of the hole relative to the surface of the airfoil. Therefore, it is intended that the present disclosure not be limited to the particular embodiment(s) disclosed as, but that the disclosure will include all embodiments falling within the scope of the appended claims.

INDUSTRIAL APPLICABILITY

Based on the foregoing, it can be seen that the present disclosure sets forth a sample sequence of steps which may decrease the time involved in inspecting target objects, specifically, by eliminating CMM inspection of master parts. Eliminating CMM inspection of master parts for use in inspecting the target objects will also increase cost savings related to material costs, yearly certification of the master parts, and labor associated with the CMM inspection.

What is claimed is:

1. A method for inspecting a plurality of target features arrayed in spaced arrangement on a surface of a target object, comprising the steps of:
   providing a fixture for holding the target object;
   providing a high speed camera;
   performing a first measurement pass,
     wherein the first measurement pass comprises the steps of:
       selectively positioning at least one of the holding fixture and the high speed camera relative to the other in an intermittent motion along a three-dimensional path over a plurality of selected target features with stationary pause;
       each time the high speed camera orientates in a stationary pause relationship to one of the selected target features, capturing a first image and determining a first location of the selected target feature during a first exposure duration using the high speed camera, the high speed camera enabling inspecting of the plurality of selected target features, intermittent stationary pause of the selected target feature relative to the high speed camera over a first duration of a first frame capture resulting in a true position tolerance of the selected target feature; and
   performing a second measurement pass,
     wherein the second measurement pass comprises the steps of:
       selectively positioning at least one of the holding fixture and the high speed camera relative to the other in continuous relative motion along the three-dimensional path over the plurality of selected target features without pause;
       each time the high speed camera orientates to one of the selected target features, capturing a second image and determining a second location of the selected target feature during a second exposure duration using the high speed camera while in relative motion, the high speed camera enabling inspecting of the plurality of selected target features without pause, movement of the selected target feature relative to the high speed camera over a second duration of a second frame capture being less than a predetermined fraction of the true position tolerance of the selected target feature.

2. The method of claim 1, further comprising the step of storing the first captured image and the first determined location of each selected target feature of the plurality of selected target features in a data archive and storing the second captured image and the second determined location of each selected target feature of the plurality of selected target features in the data archive.

3. The method of claim 2, further comprising the step of creating a correction file including respective result locations, each respective result location calculated from differences between the first determined location and the second determined location of each selected target feature of the plurality of selected target features.

4. The method of claim 3, further comprising the steps of providing a next-to-be-inspected target object in the holding fixture and performing a third measurement pass on a plurality of next-to-be-inspected target features arrayed in spaced arrangement on a surface of the next-to-be-inspected target object, wherein the third measurement pass comprises the steps of:
   selectively positioning at least one of the holding fixture and the high speed camera relative to the other in continuous relative motion along the three-dimensional path over a plurality of selected next-to-be-inspected target features without pause, and
   each time the high speed camera orientates to one of the selected next-to-be-inspected target features of the plurality of selected next-to-be-inspected target features, capturing a third image and determining a third location of the selected next-to-be-inspected target feature of the plurality of selected next-to-be-inspected target features during a third exposure duration using the high speed camera while in relative motion, the high speed camera enabling inspecting of the plurality of selected next-to-be-inspected target features without pause, movement of the selected next-to-be-inspected target feature of the plurality of selected next-to-be-inspected target features relative to the high speed camera over the third duration of a third frame capture being less than the predetermined fraction of the true position tolerance of the selected target feature.

5. The method of claim 4, further comprising the step of creating a report file in the data archive, the report file calculated by combining each determined third location of the selected next-to-be-inspected target feature of the plurality of selected next-to-be-inspected target features and each respective result location in the correction file.

6. The method of claim 1, further comprising the steps of providing a light array in operative association with the high speed camera and each time the high speed camera orientates to one of the selected target features, powering the light array to illuminate the selected target feature during one of the first exposure duration and the second exposure duration.

7. The method of claim 2, further comprising the step of creating a time-delay file including respective result times, each respective result time calculated by converting the differences between the first determined location and the second determined location of each selected target feature of the plurality of selected target features.

8. The method of claim 7, further comprising the steps of providing a next-to-be-inspected target object in the holding fixture and performing a third measurement pass on a plurality of next-to-be-inspected target features arrayed in spaced arrangement on a surface of the next-to-be-inspected target object without pause, wherein the third measurement pass comprises the steps of:
  selectively positioning at least one of the holding fixture and the high speed camera relative to the other in a next-to-be-inspected continuous relative motion along the three-dimensional path over a plurality of selected next-to-be-inspected target features without pause,
  adjusting the high speed camera with the time-delay file, and
  each time the high speed camera orientates at each respective result time of the time-delay file, capturing a third image and determining a third location of the selected next-to-be-inspected target feature of the plurality of selected next-to-be-inspected target features during a third exposure duration using the high speed camera while in relative motion, the high speed camera enabling inspecting of the next-to-be-inspected target object without pause, movement of the next-to-be-inspected target object relative to the high speed camera over a third duration of a third frame capture being less than the predetermined fraction of the true position tolerance of the selected target feature.

9. The method of claim 8, further comprising the step of storing each third image in a data archive.

10. A method for inspecting a plurality of target features arrayed in spaced arrangement on a surface of a target object, comprising the steps of:
  providing a fixture for holding the target object;
  providing a high speed camera;
  performing a first measurement pass,
    wherein the first measurement pass comprises the steps of:
      selectively positioning at least one of the holding fixture and the high speed camera relative to the other in a first continuous relative motion along a three-dimensional path over a plurality of selected target features without pause, the first continuous relative motion moving at a first speed;
      each time the high speed camera orientates to one of the selected target features, capturing a first image and determining a first location of the selected target feature during a first exposure duration using the high speed camera while in relative motion, the high speed camera enabling inspecting of the plurality of selected target features without pause, movement of the selected target feature relative to the high speed camera over a first duration of a first frame capture being less than a predetermined fraction of a true position tolerance of the selected target feature; and
  performing a second measurement pass,
    wherein the second measurement pass comprises the steps of:
      selectively positioning at least one of the holding fixture and the high speed camera relative to the other in a second continuous relative motion along the three-dimensional path over the plurality of selected target features without pause, the second continuous relative motion moving at a second speed, the second speed being less than the first speed,
      each time the high speed camera orientates to one of the selected target features, capturing a second image and determining a second location of the selected target feature during a second exposure duration using the high speed camera while in relative motion, the high speed camera enabling inspecting of the plurality of selected target features without pause, movement of the selected target feature relative to the high speed camera over a second duration of a second frame capture being less than the predetermined fraction of the true position tolerance of the selected target feature.

11. The method of claim 10, further comprising the steps of storing the first captured image and the first determined location of each selected target feature of the plurality of selected target features in a data archive and storing the second captured image and the second determined location of each selected target feature of the plurality of selected target features in the data archive.

12. The method of claim 11, further comprising the step of creating a correction file including respective result locations, each respective result location calculated by extrapolating, to a zero speed, the first determined location and the second determined location of each selected target feature of the plurality of selected target features.

13. The method of claim 12, further comprising the steps of providing a next-to-be-inspected target object in the holding fixture and performing a third measurement pass on a plurality of next-to-be-inspected target features arrayed in spaced arrangement on a surface of the next-to-be-inspected target object, wherein the third measurement pass comprises the steps of:
  selectively positioning at least one of the holding fixture and the high speed camera relative to the other in a next-to-be-inspected continuous relative motion along the three-dimensional path over a plurality of selected next-to-be-inspected target features without pause, the next-to-be-inspected continuous relative motion moving at the first speed, and each time the high speed camera orientates to one of the selected target features of the plurality of selected next-to-be-inspected target features, capturing a third image and determining a third location of the selected next-to-be-inspected target feature of the plurality of selected next-to-be-inspected target features during a third exposure duration using the high speed camera while in relative motion, the high speed camera enabling inspecting of the plurality of selected next-to-be-inspected target features without pause, movement of the selected target feature of the plurality of selected next-to-be-inspected target features relative to the high speed camera over a third duration of a third frame capture being less than the predetermined fraction of the true position tolerance of the selected target feature.

14. The method of claim 13, further comprising the step of creating a report file in the data archive, the report file calculated by combining each determined third location of the selected next-to-be-inspected target feature of the plurality of selected next-to-be-inspected target features and each respective result location in the correction file.

15. The method of claim 10, further comprising the steps of performing at least a third measurement pass, wherein the at least third measurement pass comprises the steps of:

selectively positioning at least one of the holding fixture and the high speed camera relative to the other in a third continuous relative motion along the three-dimensional path over the plurality of selected target features without pause, the third continuous relative motion moving at a third speed, the third speed being less than the second speed, each time the high speed camera orientates to one of the selected target features, capturing a third image and determining a third location of the selected target feature during a third exposure duration using the high speed camera while in relative motion, the high speed camera enabling inspecting of the plurality of selected target features without pause, movement of the selected target feature relative to the high speed camera over a third duration of a third frame capture being less than the predetermined fraction of the true position tolerance of the selected target feature.

16. The method of claim 15, further comprising the steps of storing the first through third captured images of each selected target feature of the plurality of selected target features in a data archive and storing the first through third determined locations of each selected target feature of the plurality of selected target features in the data archive.

17. The method of claim 16, further comprising the step of creating a correction file including respective result locations, each respective result location calculated by extrapolating, to a zero speed, the first through third determined locations of each selected target feature of the plurality of selected target features.

18. A method for inspecting a plurality of target features arrayed in spaced arrangement on a surface of a target object, comprising the steps of:

providing a fixture for holding the target object;

providing a high speed camera;

providing a light array in operative association with the high speed camera;

performing a first measurement pass, wherein the first measurement pass comprises the steps of:

selectively positioning at least one of the holding fixture and the high speed camera relative to the other in a first continuous relative motion along a three-dimensional path over a plurality of selected target features without pause, the first continuous relative motion moving at a first speed;

each time the high speed camera orientates to one of the selected target features, capturing a first image and determining a first location of the selected target feature during a first exposure duration using the high speed camera while in relative motion, the high speed camera enabling inspecting of the plurality of selected target features without pause, movement of the selected target feature relative to the high speed camera over a first duration of a first frame capture being less than a predetermined fraction of a true position tolerance of the selected target feature; and performing a second measurement pass, wherein the second measurement pass comprises the steps of:

selectively positioning at least one of the holding fixture and the high speed camera relative to the other in a second continuous relative motion along the three-dimensional path over the plurality of selected target features without pause, the second continuous relative motion moving at a second speed, the second speed being less than the first speed, each time the high speed camera orientates to one of the selected target features, capturing a second image and determining a second location of the selected target feature during a second exposure duration using the high speed camera while in relative motion, the high speed camera enabling inspecting of the plurality of selected target features without pause, movement of the selected target feature relative to the high speed camera over a second duration of a second frame capture being less than the predetermined fraction of the true position tolerance of the selected target feature.

19. The method of claim 18, wherein each time the high speed camera orientates to one of the selected target features, the light array is powered to illuminate the selected target feature during one of the first exposure duration and the second exposure duration.

20. The method of claim 18, wherein the light array is a plurality of light emitting diodes in operative association with the high speed camera.

* * * * *